United States Patent [19]

Eisenberg

[11] Patent Number: 5,562,732
[45] Date of Patent: Oct. 8, 1996

[54] HAIR GRAFT SUPPORT TRAY

[76] Inventor: Eric L. Eisenberg, 27 Dewbourne Avenue, Toronto, Ontario, Canada, M5P 1Z6

[21] Appl. No.: 524,223

[22] Filed: Sep. 6, 1995

[51] Int. Cl.⁶ .................. A41D 19/00; A61F 2/10
[52] U.S. Cl. .................. 623/15; 63/2; 224/217
[58] Field of Search .................. 63/15, 2; 623/15; 224/217, 218, 219, 222, 267

[56] References Cited

U.S. PATENT DOCUMENTS

| | | | |
|---|---|---|---|
| 3,596,964 | 8/1971 | Zazzara | 224/217 |
| 3,826,407 | 7/1974 | Keating | 224/219 |
| 3,933,286 | 1/1976 | Karkas | 224/219 |
| 4,136,805 | 1/1979 | Storms | 224/219 |
| 4,202,139 | 5/1980 | Hong et al. | 224/217 |
| 4,871,102 | 10/1989 | Wickersham | 224/267 |
| 4,901,847 | 2/1990 | Kesling | 224/217 |
| 5,169,315 | 12/1992 | Bull | 224/217 |
| 5,215,236 | 6/1993 | Waddell | 224/218 |
| 5,222,643 | 6/1993 | Platt | 224/218 |
| 5,368,482 | 11/1994 | Johnsen et al. | 224/217 |

*Primary Examiner*—Michael J. Milano

[57] ABSTRACT

A tissue graft holder comprises a tray having a plurality of receptors for supporting tissue grafts and a tray support comprising a ring for attachment to a finger of a user. The tray has a plurality of drainage holes extending from its upper surface. The support comprises a tray mount for releasably mounting the tray. The tray mount has a pair of opposed mounting grooves spaced such that the tray sides may be engaged by the mounting grooves so that the tray may be slidably detached from the support. The tissue graft holder is suited for use in hair transplant surgery.

12 Claims, 2 Drawing Sheets

HAIR GRAFT SUPPORT TRAY

FIELD OF THE INVENTION

The present invention is directed to a tissue graft holder, and more specifically to a tissue graft holder for use in hair transplant surgery.

BACKGROUND OF THE INVENTION

In tissue transplant surgery, grafts of tissue are typically removed from one portion of a patient's body during a graft removal step of the surgery. The grafts are then implanted to another region of the patient's body during the implant step of the surgery. In performing such surgery, it is necessary to properly transport and store the grafts removed from the patient during the removal step before their implantation. Additionally, the grafts must be made available to the surgeon so that they are readily accessible during the implant step of the surgery.

Specifically, in hair transplant surgery, the practice has been to surgically remove grafts of hair bearing tissue from the head of a patient, place the strips on a cutting surface, cut the grafts into micro- or mini-grafts and store these grafts in a liquid containing dish. Thereafter, in order to implant the micro- or mini-grafts, the surgeon typically arranges the grafts on the top surface of one of his or her gloved hands. This is typically accomplished by individually removing grafts from the liquid containing dish and placing them one-by-one on the top surface of the gloved hands. During the implant step of the surgery, the surgeon uses this hand as a support for the tissue grafts and implants the grafts using fine forceps with the remaining free hand. Because one hand is used to support the tissue grafts, the fingers of this hand are of limited use in the surgical process.

The present invention is directed at a tissue graft holder which facilitates tissue transplant surgery.

SUMMARY OF THE INVENTION

According to one aspect of the invention, there is provided a tissue graft holder, comprising a tray having a plurality of receptors for supporting tissue grafts; a tray support for attachment to an appendage of a user, said support comprising a tray mount for releasably mounting said tray.

According to another aspect of the invention, there is provided a tissue graft holder, comprising a tray having an upper surface for holding tissue grafts and a plurality of drainage holes extending from said upper surface; a tray support for attachment to an appendage of a user, said support having a tray mount extending therefrom for releasably mounting said tray.

According to yet another aspect of the present invention, there is provided a tissue graft tray comprising an upper surface having a plurality of drainage holes and a plurality of receptors for supporting tissue grafts; means to engage a tray support.

DESCRIPTION OF THE DRAWINGS

In the drawings which illustrate a preferred embodiment of the present invention.

DETAILED DESCRIPTION OF THE PREFERRED EMBODIMENTS

Figure 1:
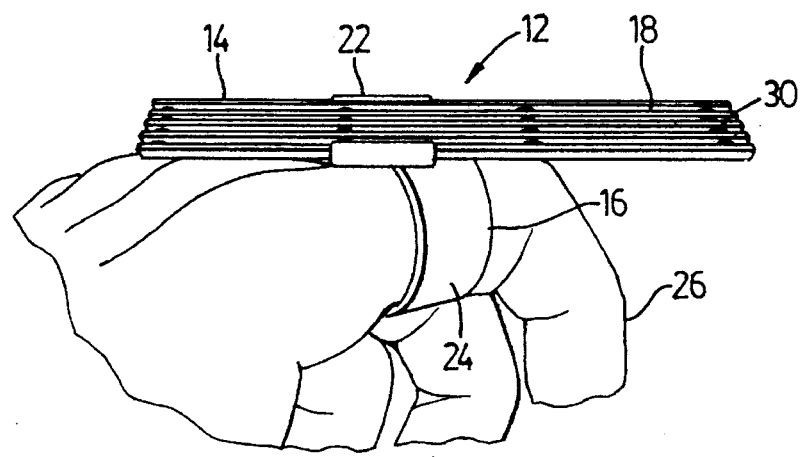
FIG. 1 is a side perspective view of a tissue graft holder in accordance with one embodiment of the present invention in place on a surgeon's hand.
Figure 2:
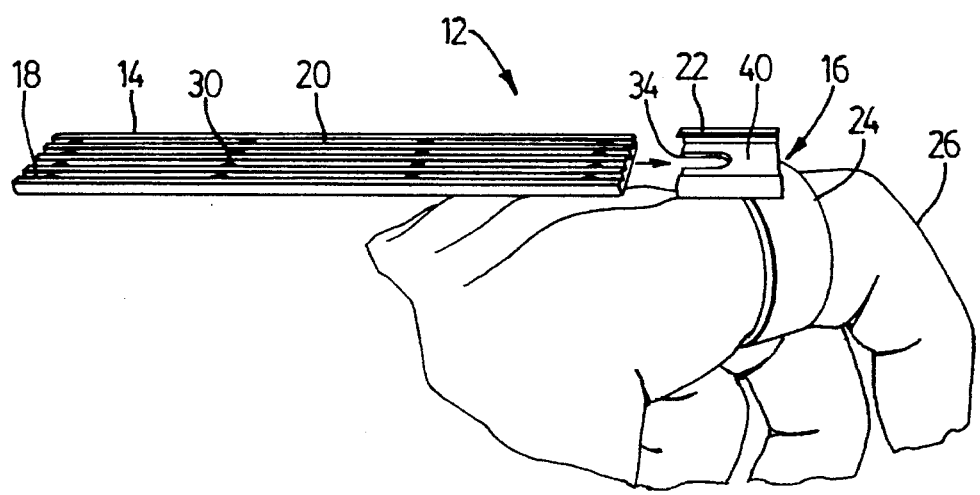
FIG. 2 is a further perspective view of the tissue graft holder of FIG. 1, shown disassembled.

With reference to FIGS. 1 and 2, a tissue graft holder 12 comprises a tray 14 and a tray support 16. Both tray 14 and tray support 16 are made of metal, preferably high grade stainless steel. Tray 14 is generally rectangular in shape and has dimensions of approximately 9 cm (length)×2 cm (width) and 0.2 cm (thickness). Tray 14 may be slidably mounted on tray support 16. Tray support 16 consist of a tray mount 22 and ring 24. Ring 24 allows attachment of tray support 16 to an appendage, for example a finger 26, of a user. Tray mount 22 extends from ring 24 and is pivotally attached to ring 24 so that the tray mount 22 may be rotated in the plane of planar platform 40 of the tray mount 22.

Figure 3:
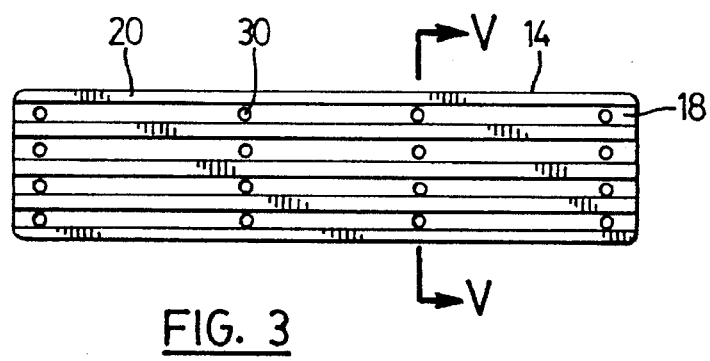
FIG. 3 is top plan view of a tissue graft tray in accordance with one embodiment of the present invention.
Figure 4:
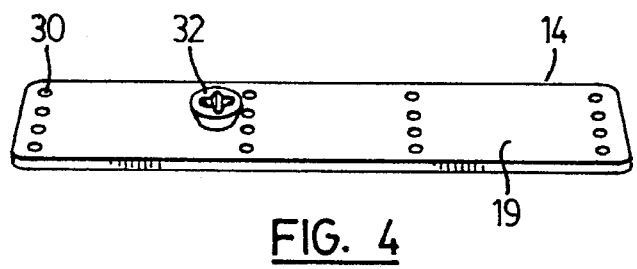
FIG. 4 is a bottom perspective view of the tissue graft tray of FIG. 3.
Figure 5:
FIG. 5 is a cross-sectional view along the lines V—V of FIG. 3.

As is shown in FIGS. 3, 4 and 5, tray 14 has a plurality of grooves 18 along an upper surface 20. Each groove 18 acts as a receptor for supporting tissue grafts and has a generally semi-circular cross section (FIG. 5). The grooves have an approximate width of 4 mm and are generally parallel and extend along the length of tray 14. Additionally, tray 14 has a number of drainage holes 30 extending from an upper surface 20 to a lower surface 19 of tray 14. Drainage holes 30 are located in grooves 18.

Extending from lower surface 19 is a protuberance 32 (FIG. 4). Protuberance 32 may, for example, be a screw which is screwed into the lower surface 19 of tray 14. Protuberance 32 is adapted to engage a notch 34 in tray mount 22 (FIG. 2).

Figure 6:
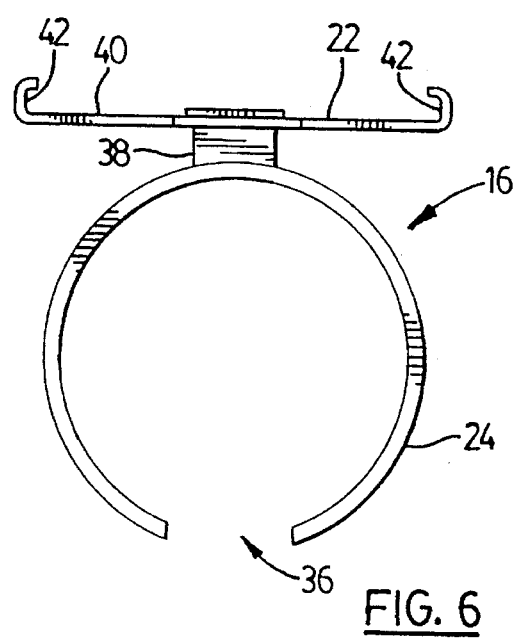
FIG. 6 is a front plan view of a tray support in accordance with one embodiment of the present invention.

As shown in FIG. 6, ring 24 has a generally O-shaped cross-section, with a minor break 36 along its circumference. This break allows ring 24 to deform slightly in the radial direction of the O-shape and thereby adapt to a number of differently sized fingers. The material chosen for ring 24 is preferably resilient so that the ring 24 will return to its original shape after having been expanded in a radial direction. Pivot pin 38 extends radially from ring 24. Pivotally mounted atop pivot pin 38 is tray mount 22. Preferably, pivot pin 38 is a rivet, allowing tray mount 22 to sit virtually flush with ring 24. Tray mount 22 has a generally planar platform 40 with two edges defining opposed U-shaped mounting grooves 42. Tray mount 22 therefore has a generally C-shaped cross section. Pivot pin 38 permits mount 22 to rotate in the plane of its generally planar platform 40.

In operation of tissue graft holder 12 in hair transplant surgery, tray support 16 and a number of trays 14 are first sterilized by, for example, applying suitable disinfectants or heated water.

A surgeon using the appropriate procedure removes several strips of skin from the patient. The strips of skin are then cut into micro- or mini-grafts. Using appropriate surgical equipment such as tweezers, the micro- or mini-grafts are placed in grooves 18 of a tray 14, which act as receptors for the grafts. At this stage, the tray 14 is typically not attached to the tray support 22. Each graft is placed in a groove so that it is longitudinally spaced from other grafts in the groove. The grooves space the grafts laterally and assist in preventing them from sliding on the tray 14. Micro- or mini-grafts are placed on a tray 14 until there is no more room on the tray 14 for further grafts. Typically, a single tray 14 will adequately support 60–80 mini-grafts. The tray 14, with the grafts, is then placed into a storage dish which contains a saline saturated gauze so that saline may wick up through the holes 30 in the tray. The grafts on the tray 14 are also dampened with a normal saline solution. The dish is then covered to prevent moisture loss and keep the grafts viable. In addition, the grafts may be chilled with ice or a suitable substitute which is placed in a separate container under the dish. A second empty tray 14 is used to receive further micro- or mini-grafts. Once the second tray 14 has been filled with grafts, it too is placed in a similar covered dish. This process is repeated until a sufficient number of grafts have been removed from the patient. Typically 300–600 mini-grafts might be used in a single operation.

Once the surgeon is ready to implant the grafts in another region on the patient's body, the surgeon places ring 24 on one of his or her fingers with the tray mount 22 facing in a direction generally away from the top of the ring-bearing hand. The surgeon then removes a tray 14 filled with micro- or mini-grafts from one of the storage dishes. In this regard, the holes 30 provide points through which fine forceps may be used to grasp the tray 14 and remove it from the storage dish. The tray 14 is then slid onto platform 40 of tray mount 22 from the end of tray mount 22 having notch 34 so that the sides of tray 14 are engaged by U-shaped mounting grooves 42 of tray mount 22. The bottom surface 19 of tray 14 is in contact with planar platform 40 of tray mount 22 and tray 14 is slid along its bottom surface 19 onto platform 40, until protuberance 32 engages notch 34. The combination of the engagement of notch 34 by protuberance 32 and the engagement of the sides of tray 14 in U-shaped mounting grooves 42 retain tray 14 in tray mount 22.

As the tissue graft holder 12 is attached to one finger of the surgeon's hand (by ring 24), the surgeon retains some use of the remaining fingers of the hand to which the graft holder is attached (FIGS. 1 and 2). For further convenience, tray 14 may be rotated about pivot pin 34 on the surgeon's hand. The grafts are implanted into incisions made at the commencement of the transplant operation. The free fingers of the hand to which the graft holder is attached may be used to hold a cotton-tipped applicator over the surface of a previously implanted graft. Once all the grafts have been removed from tray 14, tray 14 is slid off from support 16. A second tray 14 retaining grafts may be removed from a storage dish, slid onto tray mount 22 and used as a source for further grafts. Once all the grafts on the second tray 14 have been implanted, the second tray 14 is removed from support 16. This procedure is repeated until surgery is complete.

Once surgery is complete, tray mount 16 and any tray 14 attached thereto may be removed from the surgeon's finger. The used trays 14 and tray mount 16 may then be sterilized, stored and later reused.

It will be understood by a person skilled in the art that numerous modifications of this preferred embodiment are possible. For example, the tray and tray support need not be made of stainless steel, but may be made of a rigid plastic. Thus the trays and tray mount may be disposed after a single use. The grooves 18 need not have a semi-circular cross section. Alternatively, the receptors need not be grooves, but may be dimples and valleys arranged on the surface of the tray. Additionally, the tray support need not consist of a ring, but may comprise any type of mounting means, such as a band or a clip, for attaching the tray support in the proximity of an appendage of a surgeon. Similarly, any means of removably attaching the tray to the mount may be used. For example, the tray may be attached to the mount by means of snap type assembly.

It will be further understood that the invention is not limited to the illustrations described and shown herein, which are deemed to be merely illustrative of a preferred embodiment of carrying out the invention, and which are susceptible to modification of form, size, arrangement of parts and details of operation. The invention, rather, is intended to encompass all such modifications which are within its spirit and scope as defined by the claims.

I claim:

1. A tissue graft holder comprising
   a tray having a plurality of receptors for supporting tissue grafts comprising a plurality of parallel grooves, each of which has at least one drainage hole;
   a tray support for attachment to an appendage of a user, said support comprising a tray mount for releasably mounting said tray, and a ring from which said tray mount extends.

2. The tissue graft holder of claim 1 wherein said tray mount has at least one mounting groove; and
   said tray further comprising means to engage said mounting groove so that said tray may be slidably detached from said support.

3. The tissue graft holder of claim 2 wherein said tray mount is pivotally mounted on said ring, so that said tray mount may rotate in a plane parallel to tray supporting platform of said tray mount.

4. The tissue graft holder of claim 3 wherein said tray further comprises a medial protuberance for abutting said tray mount.

5. A tissue graft holder comprising
   a tray comprising an upper surface for holding tissue grafts and a plurality of drainage holes extending from said upper surface;
   a tray support comprising a ring for attachment to an appendage of a user, said support further comprising a tray mount for releasably mounting said tray;
   said tray mount comprising at least one mounting groove and said tray further comprising means to engage said mounting groove so that said tray may be slidably detached from said support.

6. The tissue graft holder of claim 5 wherein said tray mount is pivotally mounted on said ring, so that said tray mount may rotate in a plane parallel to tray supporting platform of said tray mount.

7. The tissue graft holder of claim 6 wherein said tray further comprises a medial protuberance for abutting said tray mount.

8. The tissue graft holder of claim 7 further comprising a plurality of receptors for supporting tissue grafts.

9. The tissue graft holder of claim 8 wherein said plurality of receptors comprises a plurality of parallel grooves.

10. The tissue graft holder of claim 9 wherein said tray mount has two opposed mounting grooves forming a C-shaped channel for reception of said tray, said tray having sides engaging said mounting grooves, said tray mount having a notch for reception of said medial projecting abutment.

11. A tissue graft tray comprising
    an upper surface and a bottom surface, said upper surface comprising a plurality of parallel grooves, each groove having a drainage hole extending from said upper surface to said bottom surface and;
    means to engage a support tray.

12. The tissue graft tray of claim 11
    wherein said plurality of receptors further comprises a plurality of parallel grooves.

* * * * *